United States Patent [19]

Oehr et al.

[11] Patent Number: 5,264,623

[45] Date of Patent: Nov. 23, 1993

[54] METHOD OF PRODUCING CALCIUM SALTS FROM BIOMASS

[75] Inventors: Klaus H. Oehr, Surrey; Donald S. Scott, Waterloo, both of Canada; Stefan Czernik, Lakewood, Colo.

[73] Assignee: Energy Mines & Resources Canada, Ottawa, Canada

[21] Appl. No.: 115

[22] Filed: Jan. 4, 1993

[51] Int. Cl.$^5$ .............................................. C07C 51/00
[52] U.S. Cl. .................................................. 562/515
[58] Field of Search ............... 562/523, 525, 607, 608, 562/515

[56] References Cited

U.S. PATENT DOCUMENTS

| | | | |
|---|---|---|---|
| 939,980 | 11/1909 | Chute | 562/608 X |
| 969,635 | 9/1910 | Kennedy et al. | 562/607 |
| 1,276,643 | 8/1918 | Gendreau | 562/607 |
| 1,608,075 | 11/1926 | Wallin | 562/523 X |
| 2,290,157 | 7/1942 | Bright | 202/56 |
| 2,358,229 | 9/1944 | Isham et al. | 260/344 |
| 2,461,740 | 2/1949 | Kiebler | 562/523 X |
| 2,551,675 | 5/1951 | Hillyer et al. | 562/523 |
| 2,722,546 | 11/1955 | Toland, Jr. | 562/523 X |
| 2,878,283 | 1/1957 | Othmer | 260/541 |
| 3,298,928 | 1/1967 | Esterer | 201/6 |
| 3,562,319 | 2/1971 | Brink | 562/515 |
| 4,088,660 | 5/1978 | Pourunes | 562/515 |
| 4,401,514 | 8/1983 | Kanzler et al. | 203/15 |
| 4,553,978 | 11/1985 | Yvan | 562/515 X |
| 4,670,613 | 6/1987 | Ruyter et al. | 585/240 |
| 4,880,473 | 11/1989 | Scott et al. | 127/37 |
| 4,897,497 | 1/1990 | Fitzpatrick | 562/515 X |
| 4,935,567 | 6/1990 | Yokoyama et al. | 585/240 |

Primary Examiner—Arthur C. Prescott

[57] ABSTRACT

Calcium salts, such as calcium acetate, calcium formate or calcium proprionate, are obtained from aqueous liquors derived from the pyrolysis of lignocellulosic biomass containing cellulose, hemicelluloses or starch. The above biomass is subjected to rapid pyrolysis to obtain a crude product containing an aqueous phase and an organic phase. The product obtained, preferably as the aqueous phase, is then distilled to produce a distillate containing at least one acid selected from acetic acid, formic acid and propionic acid as well as their esters and formaldehyde. An alkaline source of calcium is added to this distillate to adjust the pH to an alkaline level sufficient to hydrolyze the esters, cause at least partial oxidation of the formaldehyde and prevent volatilization of acetate, formate or propionate ions as acetic acid, formic acid or propionic acid respectively. This pH adjusted alkaline liquid is then subjected to a further distillation to remove water and volatile organic components and produce at least one of calcium acetate, calcium formate and calcium propionate as solid residue.

9 Claims, No Drawings

METHOD OF PRODUCING CALCIUM SALTS FROM BIOMASS

FIELD OF INVENTION

This invention relates to methods for producing calcium salts such as calcium acetate, calcium formate or calcium propionate from aqueous liquors derived from the pyrolysis of lignocellulosic biomass containing cellulose, hemicelluloses, or starch.

DESCRIPTION OF THE PRIOR ART

The prior art has described a need for low cost calcium acetate, calcium formate and calcium propionate salts for a variety of applications. For instance Durych et al. (Calcium Magnesium Acetate, An Emerging Bulk Chemical for Environmental Applications, Elsevier, N.Y., pages 293-296) showed that calcium acetate was superior to calcium carbonate for the purpose of scrubbing sulphur dioxide. Yoon in U.S. Pat. No. 4,615,871 describes a process for reducing the sulphur dioxide content of flue gas by injection of calcium acetate or calcium formate solution into the stack. Sharma (Calcium Magnesium Acetate, An Emerging Bulk Chemical for Environmental Applications, Elsevier, N.Y., pages 273-284) describes the use of calcium acetate solutions to impregnate coals prior to combustion as a means for sulphur emissions control.

Gancy in U.S. Pat. No. 4,377,488 describes the preparation of calcium acetate for the purpose of deicing. He states "When calcium acetate and calcium magnesium acetate are prepared by straightforward neutralization of acetic acid by the appropriate calcium bases, the predominant cost factor is the relatively high cost of the raw material acetic acid. Any commercial development plans would therefore have to include a search for the cheapest available source of acid, such as industrial waste streams for example". However, the author does not reduce to practise a cheaper source of acetic acid. Ray and Thomas in Canadian patent 1072134 describe the use of calcium formate for producing improved cement compositions. Bertram et al. in United Kingdom patent 1515487 describe the use of calcium formate as an additive in the preparation of silage.

Calcium acetate, calcium formate and calcium propionate are manufactured from commercially available acetic acid, formic acid and propionic acid by reactions such as the following:

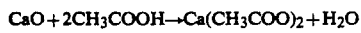
$$CaO + 2CH_3COOH \rightarrow Ca(CH_3COO)_2 + H_2O$$

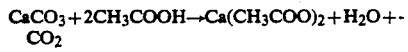
$$CaCO_3 + 2CH_3COOH \rightarrow Ca(CH_3COO)_2 + H_2O + CO_2$$

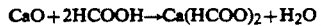
$$CaO + 2HCOOH \rightarrow Ca(HCOO)_2 + H_2O$$

$$CaCO_3 + 2HCOOH \rightarrow Ca(HCOO)_2 + H_2O + CO_2$$

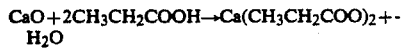
$$CaO + 2CH_3CH_2COOH \rightarrow Ca(CH_3CH_2COO)_2 + H_2O$$

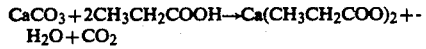
$$CaCO_3 + 2CH_3CH_2COOH \rightarrow Ca(CH_3CH_2COO)_2 + H_2O + CO_2$$

In the prior art, the high cost of producing calcium acetate, calcium formate and calcium propionate is attributed to the excessive cost of the carboxylic acid raw material. For instance the Jul. 15, 1991 issue of the Chemical Marketing Reporter quotes $0.94/lb ($1880/ton) for calcium acetate even though the cost of the calcium oxide (lime) raw material is only $52-72/-ton. It is estimated that 80% of the cost of calcium magnesium acetate (CMA) is tied to the cost of acetic acid (Chemical Week, Feb. 1, 1989, page 19).

Shemeryankina and Mitereva (Russian Pharmaceutical Chemistry Journal 1975:565-566) describe a method of preparing calcium acetate from waste liquids containing the acetate anion, for example, the wastes from the production of levomytecin, phenacetin and $\gamma$-aminobutyric acid. For instance, the mother liquors obtained in the manufacture of phenacetin contain 15-18% acetic acid, 2-4% organic impurities, and 78-83% water. To 500 mL of waste liquid were added 70 g lime to pH 7.5-8.0. Water (340 mL) was distilled from the solution. The residue was dried and yielded 100 g of calcium acetate. The yield of calcium acetate powder was 95%. Although the Russian reference provides a source of calcium acetate derived from waste, this source of calcium acetate is insufficient to supply the large demand for calcium acetate in sulphur dioxide control, cement manufacture, surface deicing and silage production. It requires the co-production of pharmaceuticals which have a limited market.

The prior art has more recently attempted to develop cheaper sources of acetic acid such as those derived from thermochemical or biochemical treatment of biomass. For example, a paper presented at the IGT Conference, Energy from Biomass and Wastes XI, Mar. 18, 1987, Orlando, Fla., by L. R. Hudson of the New York State Energy Research and Development Authority, Albany, N.Y. described attempts to produce CMA from low grade biomass in which biomass is fermented in the presence of calcium or magnesium ions and the fermentation liquor is dehydrated by evaporation to produce anhydrous alkali metal acetate salt (e.g. CMA).

Wise and Augenstein (Solar Energy Vol. 41, No. 5, 1988, pages 453-463) suggested that dilute acetic acid could be produced by the anaerobic fermentation of suitably pretreated cellulosic residues. The dilute acetic acid could be recovered from the fermentation broth using continuous liquid ion exchange extraction. The acetic acid could be separated into an aqueous medium and then contacted with lime (calcium hydroxide) to produce calcium acetate. Approaches based on fermentation utilising cellulosic biomass feedstocks suffer from the following disadvantages:

1. The cellulosic biomass generally requires exotic pretreatment, such as steam explosion, to render the cellulose susceptible to fermentation.
2. Acetic acid concentrations above 4% cannot be easily achieved due to the low tolerance of the fermenting micro-organisms to acetate ions or acetic acid.
3. Fermentation processes generate acetic acid or acetate ions slowly, resulting in high capital costs associated with large processing equipment required for prolonged process steps.
4. Fermentation processes generate large volumes of dilute aqueous waste.

It is the object of the present invention to develop simpler and less expensive methods for producing calcium salts from biomass, particularly without using fermentation technology.

SUMMARY OF THE INVENTION

This invention relates to a process for recovering calcium formate, propionate or acetate from biomass. According to the invention, a cellulose-, hemicelluloseor starch-containing biomass is subjected to rapid pyrolysis to obtain a crude product containing an aqueous phase and an organic phase. The product obtained, preferably as the aqueous phase, is then distilled to produce a distillate containing at least one acid selected from acetic acid, formic acid and propionic acid as well as their esters and formaldehyde. An alkaline source of calcium is added to this distillate to adjust the pH to an alkaline level sufficient to hydrolyze the esters, cause at least partial oxidation of the formaldehyde and prevent volatilization of acetate, formate or propionate ions as acetic acid, formic acid or propionic acid respectively. For this purpose, the pH is adjusted to a level sufficient to prevent volatilization of acetate, formate or propionate as acetic acid, formic acid or propionic acid respectively. The pH is preferably above 7, but preferably sufficiently low as to avoid residual unreacted alkaline calcium in the calcium salt. A pH range of 7.8 to 8.0 is particularly preferred. This pH adjusted alkaline liquid is then subjected to a further distillation to remove water and volatile organic components and produce at least one of calcium acetate, calcium formate and calcium propionate as solid residue.

There was substantial production of acetate and formate during the second distillation step and this was unexpected. It is believed that this can be attributed to the alkaline hydrolysis of volatile esters contained in the first distillate due the following reaction:

formate/acetate/propionate ester+alkali+heat→ alkali formate/acetate/propionate+alcohols or oxidation of formaldehyde contained in the first distillate due to the following reaction:

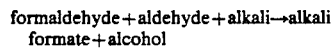
formaldehyde+aldehyde+alkali→alkali formate+alcohol

Wood is the typical biomass for the purpose of this invention. However, other biomasses, such as bark, straw, chaff, peat, seed hulls, plant stocks, corn residues etc. may be used.

It is important for achieving the results of the present invention that the pyrolysis used be a rapid pyrolysis, e.g. flash pyrolysis. Thus, the flash pyrolysis condensates of the present invention have different compositions from those obtained by ordinary destructive distillation of wood in that they appear to be rich in formic acid and esters or aldehydes which give unexpectedly high yields of acetic acid, formic acid and propionic acid during alkali assisted hydrolysis or oxidation to produce calcium carboxylate salts.

The conditions of the rapid pyrolysis step should be such as to yield a maximum amount of liquid or semi-liquid product. Such conditions are met, for instance, by a fast pyrolysis carried out in a fluidized bed reactor where a fluidized bed of sand or other inert solid is used in a mixture with the biomass, or another reactor where the residence time of pyrolysis vapours is very short. Advantageously, the pyrolysis is carried out in the fluidized bed reactor under continuous conditions. In a typical flash pyrolysis, the temperature is in the range of 400°-600° C. and the pyrolysis is typically carried out at atmospheric pressure. Details of such rapid pyrolysis of biomass is described in Scott et al, U.S. Pat. No. 4,880,473, the content of which is incorporated herein by reference.

According to a preferred embodiment of the invention, the dry residue obtained and containing calcium acetate, calcium formate or calcium propionate is washed with a solvent to remove organic impurities and increase the concentration of the calcium formate, acetate or propionate in the salt, followed by drying to remove residual solvent or moisture from the salt. A typical solvent for this purpose is alcohol, such as methanol.

According to a further preferred embodiment of the invention, the spent solvent used to remove organic impurities from the calcium is recovered for reuse by distillation or evaporation and the solvent residue is incinerated to recover calcium oxide. The calcium oxide is the preferred source of calcium.

According to another preferred embodiment, the alkaline liquor obtained following the pH adjustment is treated with a miscible organic solvent, such as acetone, which reduces the solubility of the calcium acetate, formate or propionate in the alkaline solution and causes these compounds to precipitate so that they can be recovered by simple solid-liquid separation, followed by drying to remove residual moisture or solvent. In this alternative embodiment, it is also desirable to recover the spent liquor from the aqueous alkaline liquor by distillation so that it may be reused.

According to yet another preferred embodiment of this invention, it is in some instances possible to avoid the first distillation stage by utilizing as the starting material a hydroxyacetaldehyde-stripped aqueous flash pyrolysis liquor. This product can be raised to an alkaline pH and then distilled as the second stage distillation described above. The hydroxy-acetaldehyde can be separated by precipitation as described in Stradal et al, International Publication WO91/14379, published Oct. 3, 1991, and incorporated herein by reference.

DESCRIPTION OF THE PREFERRED EMBODIMENTS

The invention will now of the following non-limiting examples.

Example 1

Western hemlock and ammabalis fir hog fuel particles (1 mm) were pyrolysed at 457°-500° C. (see Elliot et al., Energy and Fuels, 1991, Volume 5, page 400, references 12-14, 21). The hog fuel contained 12% moisture by weight. Pyrolysis products were 30.9% aqueous phase liquid and 30.2% organic phase liquid based on the input hog fuel weight. Remaining products included solid char and gas. The aqueous and organic pyrolysis liquors separated without addition of water.

Calcium acetate/formate/propionate salt was successfully prepared from the aqueous flash pyrolysis liquor as follows:

(a) Aqueous pyrolysis liquor was filtered through Whatman #1 filter paper to give 250 mL filtrate (276.94 g).

(b) This filtrate was distilled with nitrogen bleed at 22 mbar pressure to give 186.04 g distillate, and 83.67 g solid residue i.e. 97.4% product recovery. The solid residue had a calorific value of 8854 BTU/lb (4921 cal/g).

(c) Part of the distillate (151.36 g) was mixed with 6.14 g CaO to give a pH 8.0 liquor and then distilled at 22 mbar pressure as before. This distillation gave 14.97 g crude salt residue and 136.40 g distillate i.e. 96.1% product recovery. The crude salt was found to have the following % composition by weight:

| | |
|---|---|
| Calcium | 22.4 |
| Acetate | 39.4 |
| Formate | 10.4 |
| Propionate | 1.6 |
| Water | 6.8 |
| Other | 19.4 |
| Total: | 100.0 |

(d) The salt from (c) (10.105 g) was stirred with 35 mL methanol for 10-15 min and then filtered through #42 Whatman filter paper. The filter paper residue was washed with a further 35 mL methanol. The filter paper residue (single washed salt) was dried at 105° C. and weighed (7.33 g). The single washed salt was found to have the following % composition by weight:

| | |
|---|---|
| Calcium | 24.2 |
| Acetate | 48.7 |
| Formate | 12.1 |
| Propionate | 2.0 |
| Water | 8.6 |
| Other | 4.4 |
| Total: | 100.0 |

(e) The single washed salt from 4. (5.719 g) was stirred with 25 mL methanol for 10-15 min and filtered through #42 Whatman filter paper. The resulting residue was rewashed with 2 additional 25 mL aliquots of methanol. The resulting solid was dried at 105° C. and weighed (4.977 g). The purified salt was found to have the following % composition by weight:

| | |
|---|---|
| Calcium | 23.8 |
| Acetate | 52.7 |
| Formate | 13.9 |
| Propionate | 2.0 |
| Water | 5.7 |
| Other | 1.9 |
| Total: | 100.0 |

Table 1 below illustrates the increase/decrease of acetate/formate/propionate in the process liquor or salt at each processing step described in Example 1 expressed as a percentage of the starting aqueous pyrolysis liquor. Figures in brackets illustrate the increase/decrease of acetate/formate/propionate in each salt containing stream relative to its immediate predecessor.

TABLE 1

Production or Loss of Acetate/Formate/Propionate During Various Stages of Salt Production from Aqueous Fast Pyrolysis Liquor

| | Acetate | Formate | Propionate |
|---|---|---|---|
| Aqueous Pyrolysis Liquor | 100.0 | 100.0 | 100.0 |
| First Distillate | 80.2 | 59.8 | 96.7 |
| Crude Salt Residue from Second Distillation | 97.5 (121.6) | 79.7 (133.3) | 96.7 (100.0) |
| Single Washed Salt | 87.5 (89.7) | 67.2 (84.3) | 93.1 (96.3) |
| Double Washed Salt | 82.4 (94.2) | 66.8 (99.4) | 76.7 (82.4) |

The above results indicate the following:

(a) Some acetic acid, formic acid and propionic acid are lost during the first vacuum distillation.

(b) There is substantial unexpected net production of acetic acid and formic acid during the second vacuum distillation with no loss of propionic acid.

(c) Non-carboxylate organics plus water are removed from the crude salt (second distillation residue) by washing it with methanol at room temperature followed by drying.

(d) The first distillation residue has a very high heating value comparable to subbituminous coal.

As mentioned above, the substantial production of acetate and formate during the second distillation step may be due to alkaline hydrolysis of volatile esters contained in the first distillate due to the following reaction:

formate/acetate/propionate ester + alkali + heat → alkali formate/acetate/propionate + alcohols or oxidation of formaldehyde contained in the first distillate due to the following reaction:

formaldehyde + aldehyde + alkali → alkali formate + alcohol

This formaldehyde decomposition reaction is described in Morrison and Boyd (Organic Chemistry, Second Edition, 1966, p. 644, Allyn and Bacon Inc.). Bracketed figures in Table 1 suggest that ester hydrolysis is highest for formate esters followed by acetate esters and propionate esters. Published equilibrium constants for acids indicate acid strengths as follows: formic > acetic > propionic (e.g. CRC Handbook of Chemistry and Physics, CRC Press). Hine reported that the esters of strong acids are hydrolyzed more readily than weak acids (Physical Organic Chemistry, McGraw Hill, 1956, page 274). For instance, he reported the relative hydrolysis rates of methyl esters as follows: formate 223, acetate 1, propionate 0.146. Also, phenyl substituted acetates hydrolyze faster than alkyl substituted acetates. Loss of acetic acid, formic acid and propionic acid during our first stage distillation can be attributed in part to formation of non-volatile esters as follows:

carboxylic acid + alcohol (or phenol) → ester + water

Morrison and Boyd (Organic Chemistry, Second Edition, 1966, p. 603, Allyn and Bacon Inc.) indicated that this equilibrium is favoured if water is removed during the reaction.

Example 2

Calcium acetate/formate/propionate deicer (142 g) was successfully prepared from hydroxyacetaldehyde (HAA) stripped aqueous flash pyrolysis liquor (1 Litre), containing 13.5% acetic acid and 3.4% formic acid by weight, as follows (see International Publication WO 91/14379, incorporated herein by reference, for details on production of HAA stripped pyrolysis liquor):

(a) HAA stripped biomass pyrolysis liquor (250 mL, 260.11 g) was distilled with air bleed at 22 mbar pressure to give 249.12 g distillate and 6.72 g non-distillable liquid, i.e., 1.6% mass loss on distillation.

(b) Part of the distillate (215.83 g) was mixed with 29.36 g CaO to give a pH 8.0 liquor and then distilled at 50-70 mbar pressure. The distillation gave 73.57 g crude salt residue and 183.58 g distillate, i.e., 0.5% mass loss on distillation. The crude salt had the following composition (%) by weight:

| | |
|---|---|
| Calcium | 24.9 |
| Acetate | 39.4 |
| Formate | 9.8 |
| Water | 5.1 |
| Other | 20.8 |
| Total: | 100.0 |

(c) The crude salt (5.43 g) was stirred with 25 mL methanol for 20–30 min at room temperature and then passed through #40 Whatman filter paper. The filtered solid was washed with a further 2×25 mL methanol, dried at 105° C. and weighed (3.08 g). This salt had the following composition (%) by weight:

| | |
|---|---|
| Calcium | 27.2 |
| Acetate | 49.5 |
| Formate | 12.3 |
| Water | 5.9 |
| Other | 5.1 |
| Total: | 100.0 |

(d) A portion of the dried, semi-pure salt (2.06 g) from the previous step was stirred with 25 mL methanol at room temperature for 20–30 min and filtered through #40 Whatman paper. The resulting residue was re-washed with methanol (2×25 mL) and the resulting solid was dried at 105° C. and weighed (1.51 g). The purified salt had the following composition (%) by weight:

| | |
|---|---|
| Calcium | 28.1 |
| Acetate | 49.6 |
| Formate | 13.0 |
| Water | 4.3 |
| Other | 5.0 |
| Total | 100.0 |

The following Table 2 illustrates the increase/decrease %of acetate/formate/propionate in the salt-containing stream at each processing step expressed as a percentage of the starting aqueous pyrolysis liquor. Figures in brackets illustrate the increase/decrease of acetate/formate/propionate content of a salt containing stream relative to its immediate predecessor.

| | Acetate | Formate |
|---|---|---|
| Aqueous Pyrolysis Liquor | 100.0 | 100.0 |
| First Distillate | 100.3 | 96.6 |
| Crude Salt Residue from Second Distillation | 95.2 (94.9) | 94.3 (97.6) |
| Single Washed Salt | 67.6 (71.0) | 67.0 (71.1) |
| Double Washed Salt | 49.9 (73.8) | 52.2 (77.8) |

The above results indicate the following:
(a) It should be possible to produce salt from HAA-stripped biomass pyrolysis liquor without distillation prior to calcium oxide addition, since it contains no solid residue prior to calcium oxide addition. This should increase recovery of formic acid as calcium formate and eliminate one processing step. This should dramatically improve the economics for salt production. The HAA-stripped liquor is a superior raw material to unfractionated biomass pyrolysis liquor since it has a very high acid concentration (13.5% w/w acetic acid and 3.4% w/w formic acid).

(b) Non-formate/acetate organics are removed from the salt by washing it with methanol followed by drying.

EXAMPLE 3

Calcium acetate/formate salt was successfully prepared from HAA-stripped aqueous pyrolysis liquor, described in Example 2 as follows:

(a) HAA-stripped pyrolysis liquor (219.46 g) was mixed with 26.68 g CaO to five a pH 8.0 liquor and then distilled at 22 mbar pressure. The distillation gave 67.09 g crude salt residue and 176.49 g distillate, i.e., 1.0% mass loss on distillation. The crude salt had the following composition (%) by weight:

| | |
|---|---|
| Calcium | 21.8 |
| Acetate | 32.8 |
| Formate | 10.1 |
| Water | 5.3 |
| Other | 30.0 |
| Total: | 100.0 |

(b) The crude salt (10.00 g) was stirred with 35 mL methanol at 20° C. for 20 min at room temperature and then passed through #40 Whatman filter paper. The filtered solid was washed with methanol (2×25 mL), dried at 105° C. and weighed (6.60 g). This salt had the following composition (%) by weight:

| | |
|---|---|
| Calcium | 25.1 |
| Acetate | 47.4 |
| Formate | 13.3 |
| Water | 6.4 |
| Other | 7.8 |
| Total: | 100.0 |

(c) The crude salt from step (a) above (10.00 g) was stirred with 35 mL methanol at 3° C. for 20 minutes and then passed through #40 Whatman filter paper. The filtered solid was washed with methanol (2×25 mL), dried at 105° C. and weighed (7.16 g). This salt had the following composition (%) by weight:

| | |
|---|---|
| Calcium | 24.5 |
| Acetate | 43.2 |
| Formate | 11.8 |
| Water | 6.6 |
| Other | 13.9 |
| Total: | 100.0 |

The following Table 3 illustrates the increase/decrease of acetate/formate/propionate in the salt-containing stream at each processing step expressed as a percentage of the starting aqueous pyrolysis liquor. Figures in brackets illustrate the increase/decrease of acetate/formate/propionate content of a salt containing stream relative to its immediate predecessor.

TABLE 3

| | Acetate | Formate |
|---|---|---|
| Aqueous Pyrolysis Liquor | 100.0 | 100.0 |
| Crude Salt Residue from Distillation | 75.3 | 92.8 |
| Methanol Washed Salt | 71.7 | 80.7 |

TABLE 3-continued

|  | Acetate | Formate |
|---|---|---|
| (20° C.) | (95.2) | (87.0) |
| Methanol Washed Salt | 71.1 | 77.1 |
| (3° C.) | (94.4) | (83.1) |

The above results indicate the following:

HAA-stripped pyrolysis liquor is an excellent raw material for calcium acetate/formate production since it can be processed directly with calcium oxide without a prior distillation step and has a moderate water content of 68.8%. One kilogram of HAA-stripped pyrolysis liquor produced 305.7 g crude salt, 201.8 g refined salt after 20° C. methanol washing and 218.9 g refined salt after methanol washing at 3° C. The HAA-stripped liquor is a superior raw material to unfractionated biomass pyrolysis liquor since it has a very high acid concentration (13.5% w/w acetic acid and 3.4% w/w formic acid).

(b) Methanol washing of the crude salt at 20° C. results in a higher purity salt than methanol washing at 3° C. with about 10% loss in salt yield.

Example 4

In this experiment, pyrolysis liquor was the entire aqueous phase obtained from vacuum pyrolysis of a softwood and bark mixture (mainly spruce). This is not equivalent to a fast or rapid pyrolysis liquor. It contained 1.39% formic acid, 1.42% acetic acid and 82.6% water respectively.

Calcium acetate/formate salt was successfully prepared from this aqueous pyrolysis liquor as follows:

(a) The aqueous liquor was filtered through Whatman #1 filter paper to give 250 mL filtrate (258.50 g).

(b) This filtrate was distilled with nitrogen bleed at 22 mbar pressure to give 224.52 g distillate, and 19.11 g solid residue, i.e. 5.6% mass loss on distillation. The solid residue had a calorific value of 4703 cal/g.

(c) Part of the distillate (150.91 g) was mixed with 2.23 g CaO to give a pH 8 liquor and then distilled at 22 mbar pressure as before. The distillation gave 6.51 g crude deicer residue and 143.51 distillate i.e. 2.0% mass loss on distillation. The crude salt was found to have the following % composition by weight:

| Calcium | 20.0 |
|---|---|
| Acetate | 38.4 |
| Formate | 12.6 |
| Propionate | 2.9 |
| Water + other | 26.1 |
| Total: | 100.0 |

(d) The crude salt from (c) (4.43 g) was stirred with 37 mL methanol for 10-15 min and then filtered through #42 Whatman filter paper. The filter paper residue was washed with a further 37 mL methanol. The filter paper residue (single washed salt) was dried at 105° C. and weighed (7.33 g). The single washed salt was found to have the following % composition by weight:

| Calcium | 25.7 |
|---|---|
| Acetate | 45.0 |
| Formate | 19.0 |
| Propionate | 2.9 |
| Water + other | 7.4 |
| Total: | 100.0 |

(e) The single washed salt from step (d) (1.78 g) was stirred with 37 mL methanol for 10-15 min and filtered through #42 Whatman filter paper. The resulting residue was rewashed with an additional 37 mL aliquot of methanol. The resulting solid was dried at 105° C. and weighed (1.24 g). The purified salt was found to have the following % composition by weight:

| Calcium | 26.1 |
|---|---|
| Acetate | 43.0 |
| Formate | 18.2 |
| Propionate | 2.2 |
| Water + other | 10.5 |
| Total: | 100.0 |

Table 4 below illustrates the increase/decrease of acetate/formate/propionate in the process liquor or salt at each processing step described in Example 1 expressed as a percentage of the starting aqueous pyrolysis liquor. Figures in brackets illustrate the increase/decrease of acetate/formate/propionate in each deicer containing stream relative to its immediate predecessor.

TABLE 4

Production or Loss of Acetate/Formate/Propionate During Various Stages of Salt Production from Vacuum Pyrolysis Liquor

|  | Acetate | Formate | Propionate |
|---|---|---|---|
| Aqueous Pyrolysis Liquor | 100.0 | 100.0 | 100.0 |
| First Distillate | 90.5 | 77.0 | 80.6 |
| Crude Salt Residue from | 90.3 | 61.0 | 77.8 |
|  | (99.8) | (79.2) | (96.5) |
| Second Distillation Single Washed Salt | 54.6 | 47.5 | 41.7 |
|  | (60.5) | (77.9) | (53.6) |
| Double Washed Salt | 36.7 | 32.0 | 22.2 |
|  | (67.2) | (67.4) | (53.2) |

Example 5

(a) Total pyrolysis liquor (1066.11 g) derived from pyrolysis of IEA poplar, was distilled in a rotary evaporator at 75° C. and 1.5-3 mm mercury pressure to yield a distillate (297.9 g). High pressure liquid chromatographic analysis of the distillate revealed the following composition by weight: hydroxyacetaldehyde 0.5%, formic acid 1.7%, acetic acid 9.1%, acetol 2.9%. Karl Fischer water analysis indicated a water content of 82.5% by weight.

(b) The distillate from step (a) above (100.43 g) was mixed with CaO (6.25 g) to achieve a pH of 7.8.

(c) The resulting liquor from step (b) above was distilled at 22 mbar pressure to produce distillate (85.16 g) and a solid residue (16.24 g).

(d) The solid residue from step (c) above was dried at 105° C. to produce crude salt (15.53 g).

(e) This crude salt was then purified with varying quantities of methanol using a variety of techniques.

Example 6

For this study the TL #47 pyrolysis product of Brockville poplar was chosen because of its relatively high acid content. This wood sample was the same species as that described in Example 5 above, except that it was prepared from the whole tree so that it contained wood and bark from both the trunk and branches. It contained 27% of water, 36% of water soluble organic components and 37% of water insoluble organics (lignin). The concentration of acetic acid was about 9.5% of liquid pyrolysis product (tar).

The entire pyrolysis liquor was heated at 100°–120° C. and 40 mm Hg pressure (absolute) to evaporate the acetic and formic acid directly and minimise degradation of other pyrolysis liquor components. Distillate of 39.5% by weight of the original crude pyrolysis liquid was obtained which contained over 70% of the organic acid, plus esters. Lime was added to a pH of 7.0–8.0 to form calcium salts. To two samples of the alkaline salt solution, acetone was added to the extent of 60% by weight and 70% by weight, that is to 40 grams of salt solution 60 grams of acetone was added (60%), or to 40 grams of solution 93 grams of acetone was added (70%). After having added acetone (60% or 70% of mixture) for 2 minutes at 20°–25° C., a white precipitate of calcium acetate and calcium formate was obtained with a yield of 91% or 95% (respectively) of that in the volatile fraction (about 64% of the original acetic acid in the tar). No further treatment of the filtrate was done but the recovery of acetone appears to be easy and could be followed by isolation of the acetol.

Addition of the appropriate stoichiometric amount of magnesium acetate to the acid salt solution followed by filtration prior to precipitation by acetone would result in the production of mixtures of calcium acetate, magnesium acetate or calcium magnesium acetate, a compound which already has a market as a deicer.

We claim:

1. A process for recovering at least one of calcium formate, propionate and acetate from biomass which comprises:
    (a) subjecting cellulose-, hemicellulose- or starch-containing biomass to rapid pyrolysis to obtain a crude product containing an aqueous phase and an organic phase,
    (b) distilling the product obtained to produce a distillate containing at least one acid selected from acetic acid, formic acid and propionic acid and their esters or formaldehyde,
    (c) adding an alkaline source of calcium to said distillate to adjust the pH thereof to alkaline sufficient to hydrolyze said esters, cause at least partial oxidation of said formaldehyde and prevent volatilization of acetate, formate or propionate ions as acetic acid, formic acid or propionic acid respectively, and
    (d) further distilling the pH adjusted alkaline distillate of part (c) to remove water and volatile organic components and produce at least one of calcium acetate, calcium formate, and calcium propionate as solid residues.

2. A process according to claim 1 wherein the pH is adjusted to a level above 7.

3. A process according to claim 2 wherein the pH is adjusted to the range 7.8 to 8.0.

4. A process according to claim 1 wherein the calcium acetate, formate and propionate formed is washed with a solvent to remove organic impurities and increase the concentration of the calcium formate, acetate or propionate in the salt.

5. A process according to claim 4 wherein the solvent is an alcohol, e.g. methanol.

6. A process according to claim 4 wherein calcium oxide is recovered from the solvent and the calcium oxide is used as a source of calcium.

7. A process for recovering at least one of calcium formate, propionate and acetate from biomass which comprises:
    (a) subjecting cellulose-, hemicellulose- or starch-containing biomass to rapid pyrolysis to obtain a crude product containing an aqueous phase and an organic phase,
    (b) distilling the product obtained to produce a distillate containing at least one acid selected from acetic acid, formic acid and propionic acid and their esters or formaldehyde,
    (c) adding an alkaline source of calcium to said distillate to adjust the pH thereof to alkaline sufficient to hydrolyze said esters, cause at least partial oxidation of said formaldehyde and prevent volatilization of acetate, formate or propionate ions as acetic acid, formic acid or propionic acid respectively, and
    (d) treating the pH-adjusted alkaline distillate of part (c) with an organic solvent to reduce the solubility of calcium acetate, formate or propionate in the alkaline solution and cause them to at least partially precipitate, and
    (e) separating the calcium acetate, formate and propionate by solid/liquid separation.

8. A process according to claim 7 wherein the solvent is acetone.

9. A process for recovering at least one of calcium formate, propionate, and acetate which comprises:
    (a) obtaining as starting material a hydroxyacetaldehyde-stripped aqueous flash pyrolysis liquor,
    (b) adding an alkaline source of calcium to said pyrolysis liquor to adjust the pH thereof to a level sufficient to prevent volatilization of acetate, formate or propionate as acetic acid, formic acid or propionic acid respectively,
    (c) distilling the pH adjusted pyrolysis liquor to remove water and volatile organic components and produce at least one of calcium acetate, calcium formate and calcium propionate as solid residues.

* * * * *